(12) United States Patent
Zhou et al.

(10) Patent No.: US 10,732,086 B2
(45) Date of Patent: Aug. 4, 2020

(54) DEVICE AND METHOD FOR MEASURING MAGNITUDE OF SEEPAGE FORCE AND ITS INFLUENCE ON EFFECTIVE STRESS OF FORMATION

(71) Applicant: Xi'an Shiyou University, Xi'an, Shaanxi (CN)

(72) Inventors: Desheng Zhou, Shaanxi (CN); Peng Zheng, Shaanxi (CN); Xinru Li, Shaanxi (CN); Yafei Liu, Shaanxi (CN); Xianlin Ma, Shaanxi (CN); Meng Li, Shaanxi (CN); Jingwen Yang, Shaanxi (CN)

(73) Assignee: Xi'an Shiyou University, Xi'an (CN)

( * ) Notice: Subject to any disclaimer, the term of this patent is extended or adjusted under 35 U.S.C. 154(b) by 111 days.

(21) Appl. No.: 16/153,799

(22) Filed: Oct. 7, 2018

(65) Prior Publication Data

US 2020/0080924 A1    Mar. 12, 2020

(30) Foreign Application Priority Data

Sep. 6, 2018  (CN) .......................... 2018 1 1039530

(51) Int. Cl.
| | | |
|---|---|---|
| *G01B 21/32* | (2006.01) | |
| *G01N 15/08* | (2006.01) | |
| *E21B 49/08* | (2006.01) | |
| *G01F 9/02* | (2006.01) | |

(52) U.S. Cl.
CPC ....... *G01N 15/0826* (2013.01); *E21B 49/088* (2013.01); *G01F 9/026* (2013.01)

(58) Field of Classification Search
CPC .. G01N 3/12; G01N 2203/0019; G01N 33/24; G01N 2203/0048; G01N 2203/0232; G01N 2203/0226; G01N 3/18; G01N 15/082; G01N 15/0806; G01N 33/18
See application file for complete search history.

(56) References Cited

U.S. PATENT DOCUMENTS

2018/0335374 A1* 11/2018 Kanj ................... G01N 15/0826
2018/0340874 A1* 11/2018 Liu ........................... G01N 3/12
2019/0234856 A1*  8/2019 Ou ......................... G01N 15/082

FOREIGN PATENT DOCUMENTS

| CN | 102253183 B | 7/2014 |
| CN | 104089823 B | 3/2016 |
| CN | 110147561 A | 8/2019 |

* cited by examiner

*Primary Examiner* — Brandi N Hopkins
(74) *Attorney, Agent, or Firm* — Wayne & Ken, LLC; Tony Hom

(57) ABSTRACT

Disclosed is a device and method for measuring the magnitude of a seepage force and its influence on effective stress of a formation. The measuring device includes a lower bearing platform having a pressure testing device fixed on an upper part thereof, and a water storage chamber mounted with a seepage water discharge pipe. A confining pressure loading chamber is mounted on the upper part of the lower bearing platform, and the lower bearing platform is used for placing a sample which has 11 measuring points distributed at equal intervals on an outer wall thereof. An upper and a lower permeable pressure-bearing steel sheet are placed on an upper and a lower end surface of the sample, respectively. The invention can improve the validity and accuracy of measurement and make the calculation result of the test more accurate.

5 Claims, 2 Drawing Sheets

US 10,732,086 B2

DEVICE AND METHOD FOR MEASURING MAGNITUDE OF SEEPAGE FORCE AND ITS INFLUENCE ON EFFECTIVE STRESS OF FORMATION

CROSS-REFERENCE TO RELATED APPLICATIONS

This application claims to Chinese Application No. 201811039530.1 with a filing date of Sep. 6, 2018. The content of the aforementioned applications, including any intervening amendments thereto, are incorporated herein by reference.

TECHNICAL FIELD

The invention relates to the technical field of oil and gas field development, in particular to a device and method for measuring the magnitude of a seepage force and its influence on effective stress of a formation.

BACKGROUND

Hydraulic fracturing is an important means for oil and gas exploitation in unconventional oil and gas reservoirs. The core idea is to rapidly increase the pressure in formation fracture by injecting a large displacement volume of high-pressure fluid into the fracture, causing the fracture to rapture and extend along the tip. However, at the same time, the high-pressure fluid will also produce fluid loss along wall surfaces of the fracture. According to the principle of force and reaction force, the fluid loss will generate an additional force near the fracture wall surfaces under higher pressure gradient which changes as the fracture surface distance changes, thus changing the original effective stress of the fractured formation. This additional force is referred to as seepage force.

At present, the concept of seepage force is only applied to soil mechanics. It is used to study the pushing, rubbing and dragging effects of fluid on soil particles along the direction of fluid flow upon seepage of the fluid through soil, which are combined to form forces acting on soil skeleton. Existing seepage force measuring devices and methods are based on soil particles. Due to the loose structure of soil particles, the effective stress change perpendicular to the fluid flow direction does not need to be considered, and the existing devices and methods are not suitable for measuring seepage force generated by hard fractured formations under the action of high-pressure fluid, making the test measurement and calculation methods unable to meet the requirements for the study of fractured formations.

In the current hydraulic fracturing test, the pore pressure in the sample is a fixed value, and there is no device or method for measuring the magnitude of the seepage force near the fracture wall surface and the effective stress of the fractured formation caused by the seepage force. In view of the fact that the seepage force measurement methods in the prior art do not take the hard fractured formation into consideration, and the hydraulic fracturing test does not study the seepage force, it cannot truly reflect the change of effective stress near the fracture wall surface during hydraulic fracturing. Therefore, a new measuring device and method are proposed to calculate the magnitude of a seepage force generated under high injection pressure and the change of effective stress of the fractured formation caused thereby.

SUMMARY

In view of the technical situation that the prior art only measures the seepage force under the soil particle model, the object of the present invention is to provide a device and method for measuring the magnitude of a seepage force and its influence on effective stress of a formation, which is applicable when a fractured formation is subjected to the seepage force.

The invention provides a device and a method for measuring the magnitude of a seepage force and its influence on effective stress of a formation. The measuring device includes a lower bearing platform having a pressure testing device fixed on an upper part thereof, and a water storage chamber mounted with a seepage water discharge pipe. A confining pressure loading chamber is mounted on the upper part of the lower bearing platform and a non-contact three-dimensional deformation measuring system is mounted outside the confining pressure loading chamber. The lower bearing platform is used for placing a sample which has 11 measuring points distributed at equal intervals on an outer wall thereof. An upper permeable pressure-bearing steel sheet and a lower permeable pressure-bearing steel sheet are placed on an upper and a lower end surface of the sample, respectively. The sample is placed inside a transparent rubber sleeve. The top of the upper permeable pressure-bearing steel sheet is provided with an axial pressure loading device which is connected with an axial pressure servo motor, the upper permeable pressure-bearing steel sheet is respectively connected with a vacuum pump and a pore pressure loading system through a steel pipe line. The confining pressure loading chamber is connected with a confining pressure loading system through a steel pipe line and a transparent observation window is arranged in one side of an outer wall of the confining pressure loading chamber. And the axial pressure servo motor, the confining pressure loading system, the pore pressure loading system, the vacuum pump, the non-contact three-dimensional deformation measuring system, a flow pressure sensor and the pressure testing device are all electrically connected with a terminal control system.

Further, the seepage water discharge pipe is equipped with a valve.

Further, the confining pressure loading chamber is composed of an outer wall and an end cover, and the end cover is provided with an exhaust valve.

Further, valves are installed on the steel pipe lines connected with the pore pressure loading system, the confining pressure loading system and the vacuum pump.

The invention relates to a method for measuring the magnitude of a seepage force and its influence on effective stress of a formation, which includes the following steps:

(1) taking underground cores with a drilling tool, selecting a core with a complete structure and processing it into a cylindrical sample with a diameter of 50 cm and a height of 100 cm, placing the sample in a confining pressure loading chamber, marking 11 points at equal intervals from top to bottom on an outer wall of the sample as measuring points, placing an upper permeable pressure-bearing steel sheet and a lower permeable pressure-bearing steel sheet having the radius as the sample on the top and bottom of the sample, respectively, and then sleeving the sample into a transparent rubber sleeve;

(2) turning on a vacuum pump to vacuumize the sample for two hours, then turning off the vacuum pump, and recording an axial initial data $L_{00}$, $L_{01}$, $L_{02}$ . . . , $L_{10}$, and a lateral initial data $D_{00}$, $D_{01}$, $D_{02}$ . . . , $D_{10}$ of respective measuring points of the sample through a non-contact three-dimensional deformation measuring system; dividing the 11 measuring points into 5 segments, calculating an axial initial amount of each segment $\lambda_1$ ($\lambda_1 = L_{01} - L_{00}$), and then calculating by analogy $\lambda_2$, $\lambda_3$, $\lambda_4$ and $\lambda_5$, and calculating a lateral initial amount of each segment $\gamma_1$ ($\gamma_1=(D_{01}+D_{00})/2$), and then calculating by analogy $\gamma_2$, $\gamma_3$, $\gamma_4$ and $\gamma_5$;

(3) starting a confining pressure loading system to inject fluid into the confining pressure loading chamber, and simultaneously opening an exhaust valve and then closing the exhaust valve until the fluid fills the confining pressure loading chamber, loading a confining pressure to a predetermined value, and keeping the confining pressure unchanged;

(4) starting an axial pressure servo motor to apply a bias voltage to the sample to a predetermined value, and keeping the bias voltage constant;

(5) recording an axial displacement amount $l_0$, $l_1$, $l_2$ . . . , $l_{10}$, and a lateral displacement amount $d_0$, $d_1$, $d_2$ . . . , $d_{10}$ of respective measuring points of the sample when the sample is stabilized after deformation, the calculation method being the same as in step (2), and calculating an axial deformation amount $L_1$, $L_2$, $L_3$, $L_4$, $L_5$, a lateral deformation amount $D_1$, $D_2$, $D_3$, $D_4$, $D_5$, and a value $F_1$ of the pressure testing device at this time by analogy;

obtaining therefore an axial strain $\varepsilon_1$ and a lateral strain $\varepsilon_3$ of respective segments of the sample under non-porous pressure loading which are respectively:

$\varepsilon_1'=(L_1-\lambda_1)/\lambda_1$, $\varepsilon_1''=(L_2-\lambda_2)/\lambda_2$, and $\varepsilon_1'''$, $\varepsilon_1''''$, $\varepsilon_1'''''$ can be obtained in the same way; and $\varepsilon_3'=(D_1-\gamma_1)/\gamma_1$, $\varepsilon_3''=(D_2-\gamma_2)/\gamma_2$, $\varepsilon_3'''$, $\varepsilon_3''''$ and $\varepsilon_3'''''$ can be obtained in the same way;

according to the formula $$\varepsilon_1 = \frac{(\sigma_1 - 2\mu\sigma_3)}{E}, \varepsilon_3 = \frac{[\sigma_3 - \mu(\sigma_1 + \sigma_3)]}{E},$$

the effective stress of the five segments of the sample can be calculated in sequence, namely ($\sigma_1'$, $\sigma_3'$), ($\sigma_1''$, $\sigma_3''$), ($\sigma_1'''$, $\sigma_1'''$), ($\sigma_1''''$, $\sigma_3''''$), and ($\sigma_1'''''$, $\sigma_3'''''$), where E is Young's modulus and $\mu$ is Poisson's ratio;

(6) starting the pore pressure loading system to inject fluid into the sample, so as to increase the injection pressure, and recording a pore pressure value $P_1$ at an inlet end of the sample;

(7) recording a pressure $P_2$ in a water storage chamber and a value $F_2$ of the pressure testing device by a flow pressure sensor after a water pressure in the water storage chamber is stabilized, which gradually increases due to the hysteresis of fluid flowing in the sample when adjusting the pore pressure loading system to inject fluid into the sample;

(8) obtaining a seepage force measurement value of the core by $J=F_1-F_2$;

(9) calculating a seepage force according to a seepage force calculation formula $J'r_w \cdot i \cdot V$, where $$i = \frac{h_1 - h_2}{l},$$

$P_1=r_w \cdot h_1$, $P_2=r_w \cdot h_2$, where $r_w$ is volume weight of water, i is pressure gradient, V is sample volume, and $h_1$ and $h_2$ are water heads corresponding to $P_1$ and $P_2$, respectively;

(10) obtaining the seepage force of J under the corresponding axial pressure, confining pressure and flow pressure gradient of the sample when $$\left|\frac{J'-J}{J}\right| < 0.01;$$

otherwise, repeating step (1) to step (9);

(11) recording and calculating an axial deformation data $L_1'$, $L_2'$ . . . , $L_5'$, and a lateral deformation data $D_1'$, $D_2'$ . . . $D_5'$ of respective segments corresponding to respective measuring points of the sample, the calculation method being the same as in step (2);

(12) obtaining therefore an axial strain $\varepsilon_{11}$ and a lateral strain $\varepsilon_{33}$ of respective segments of the sample in the process of pore pressure loading which are respectively:

$\varepsilon_{11}'=(L_1'-\lambda_1)/\lambda_1$, $\varepsilon_{11}''=(L_2'-\lambda_2)/\lambda_2$, and $\varepsilon_{11}'''$, $\varepsilon_{11}''''$, $\varepsilon_{11}'''''$ can be obtained in the same way; and $\varepsilon_{33}'=(D_1'-\gamma_1)\gamma_1$, $\varepsilon_{33}''=(D_2'-\gamma_2)/\gamma_2$, and $\varepsilon_{33}'''$, $\varepsilon_{33}''''$, $\varepsilon_{33}'''''$ can be obtained in the same way;

similarly, the effective stress of each of the five measuring segments in the presence of fluid in the pore can be calculated in sequence by formula $$\varepsilon_1 = \frac{(\sigma_1 - 2\mu\sigma_3)}{E}, \varepsilon_3 = \frac{[\sigma_3 - \mu(\sigma_1 + \sigma_3)]}{E},$$

which are respectively ($\sigma_{11}'$, $\sigma_{33}'$), ($\sigma_{11}''$, $\sigma_{33}''$), ($\sigma_{11}'''$, $\sigma_{33}'''$), ($\sigma_{11}''''$, $\sigma_{33}''''$), and ($\sigma_{11}'''''$, $\sigma_{33}'''''$); and

(13) curve-fitting an increment of the effective stress of respective measuring segments corresponding to respective measuring points generated by the seepage force, by the following formula, respectively:

$\sigma_{axial}'=\sigma_{11}'-\sigma_1'$, $\sigma_{radical}'=\sigma_{33}'-\sigma_3'$;

$\sigma_{axial}''=\sigma_{11}''-\sigma_1''$, $\sigma_{radical}''=\sigma_{33}''-\sigma_3''$;

$\sigma_{axial}'''=\sigma_{11}'''-\sigma_1'''$, $\sigma_{radical}'''=\sigma_{33}'''-\sigma_3'''$;

$\sigma_{axial}''''=\sigma_{11}''''-\sigma_1''''$, $\sigma_{radical}''''=\sigma_{33}''''-\sigma_3''''$;

$\sigma_{axial}'''''=\sigma_{11}'''''-\sigma_1'''''$, $\sigma_{radical}'''''=\sigma_{33}'''''-\sigma_3'''''$;

according to the effective stress obtained in step (13), so as to determine an effective stress change law of at different positions the sample under the seepage force of J.

Compared with the prior art, the present invention has the following advantages:

1. The existing seepage force measuring device is only applicable to loose soil where the seepage force is generated by natural seepage of water under head pressure difference and is thus not suitable for measuring seepage force generated by hard fractured formation under the action of high-pressure fluid. The present invention is suitable for measuring the magnitude of the seepage force generated by fractured formation during hydraulic fracturing.

2. In the hydraulic fracturing test of oil field, the pore pressure and effective stress are considered and calculated as fixed values. According to the invention, after the concept of formation seepage force is proposed, the effective stress generated under the action of the seepage force in the fractured stratum and gradually changing with the distance is calculated for the first time.

3. The method of obtaining the stress increment by effective stress subtraction avoids systematic errors in the experimental operation and makes the calculation result of the test more accurate.

Figure 1:
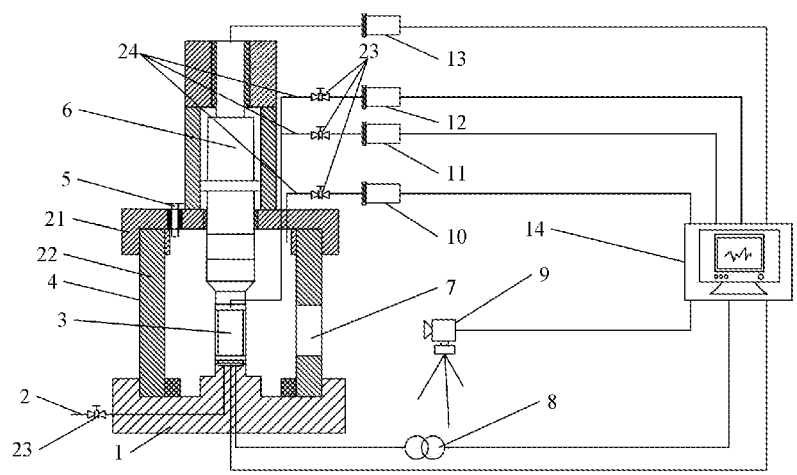
FIG. 1 is a schematic structural diagram of a measuring device according to the present invention.
Figure 2:
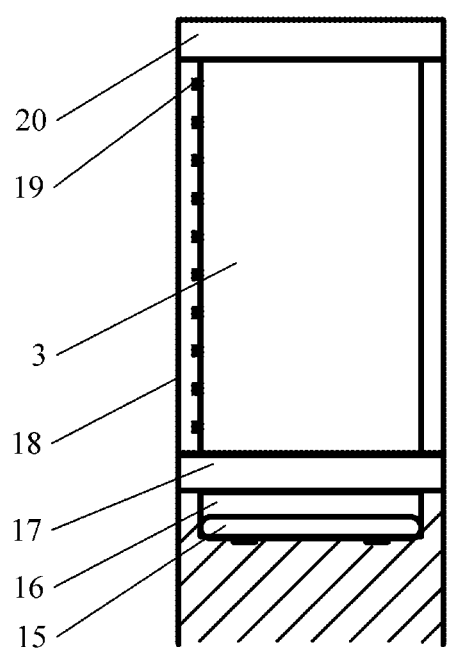
FIG. 2 is an enlarged partial view of the sample.

In the drawing: 1 lower bearing platform, 2 seepage water discharge pipe, 3 sample, 4 confining pressure loading chamber, 5 exhaust valve, 6 axial pressure loading device, 7 transparent observation window, 8 flow pressure sensor, 9 non-contact three-dimensional deformation measuring system, 10 confining pressure loading system, 11 vacuum pump, 12 pore pressure loading system, 13 axial pressure servo motor, 14 terminal control system, 15 pressure testing device, 16 water storage chamber, 17 lower permeable pressure-bearing steel sheet, 18 transparent rubber sleeve, 19 measuring point, 20 upper permeable pressure-bearing steel sheet, 21 end cover, 22 outer wall, 23 valve, 24 steel pipe line.

DETAILED DESCRIPTION

In order to make the technical problems, technical solutions and beneficial effects solved by the present invention more clear, the present invention will be further described in detail with reference to the following examples. It should be understood that the specific embodiments described herein are merely illustrative of the present invention and are not intended to limit the present invention.

The present invention will be described in further detail with reference to the drawings and specific embodiments.

The present invention relates to a device for measuring the magnitude of a seepage force and its influence on effective stress of a formation. The measuring device includes a lower bearing platform 1 having a pressure testing device 15 fixed on an upper part thereof, and a water storage chamber 16 mounted with a seepage water discharge pipe 2. A confining pressure loading chamber 4 is mounted on the upper part of the lower bearing platform, and a non-contact three-dimensional deformation measuring system 9 is mounted outside the confining pressure loading chamber 4. The lower bearing platform 1 is used for placing a sample 3 which has 10 measuring points 19 distributed at equal intervals on an outer wall thereof. An upper permeable pressure-bearing steel sheet 20 and a lower permeable pressure-bearing steel sheet 17 are placed on an upper and a lower end surface of the sample, respectively, and the sample is placed inside a transparent rubber sleeve 18. The top of the upper permeable pressure-bearing steel sheet is provided with an axial pressure loading device 6 which is connected with an axial pressure servo motor 13. The upper permeable pressure-bearing steel sheet 20 is respectively connected with a vacuum pump 11 and a pore pressure loading system 12 through a steel pipe line 24. The confining pressure loading chamber 4 is connected with a confining pressure loading system 10 through a steel pipe line 24, and a transparent observation window 7 is arranged in one side of an outer wall of the confining pressure loading chamber 4. The axial pressure servo motor 13, the confining pressure loading system 10, the pore pressure loading system 12, the vacuum pump 11, the non-contact three-dimensional deformation measuring system 9, a flow pressure sensor 8 and the pressure testing device 15 are all electrically connected with a terminal control system 14.

In this embodiment, the seepage water discharge pipe 2 is equipped with a valve 23.

In this embodiment, the confining pressure loading chamber 4 is composed of an outer wall 22 and an end cover 21, and the end cover 21 is provided with an exhaust valve 5.

In this embodiment, valves are installed on the steel pipe lines connected with the pore pressure loading system 12, the confining pressure loading system 10 and the vacuum pump 11.

The invention also relates to a method for measuring the magnitude of a seepage force and its influence on effective stress of a formation, which includes the following steps:

(1) taking underground cores with a drilling tool, selecting a core with a complete structure and processing it into a cylindrical sample 3 with a diameter of 50 cm and a height of 100 cm, placing the sample 3 in a confining pressure loading chamber 4, marking 11 points at equal intervals from top to bottom on an outer wall of the sample 3 as measuring points 19, placing an upper permeable pressure-bearing steel sheet 20 and a lower permeable pressure-bearing steel sheet 17 having the radius as the sample 3 on the top and bottom of the sample 3, respectively, and then sleeving the sample 3 into a transparent rubber sleeve 18;

(2) turning on a vacuum pump 11 to vacuumize the sample 3 for two hours, then turning off the vacuum pump 11, and recording an axial initial data $L_{00}, L_{01}, L_{02} \ldots, L_{10}$, and a lateral initial data $D_{00}, D_{01}, D_{02} \ldots, D_{10}$ of respective measuring points 19 of the sample 3 through a non-contact three-dimensional deformation measuring system 9; dividing the 11 measuring points into 5 segments, calculating an axial initial amount of each segment $\lambda_1$ ($\lambda_1 = L_{01} - L_{00}$), and then calculating by analogy $\lambda_2, \lambda_3, \lambda_4$ and $\lambda_5$, and calculating a lateral initial amount of each segment $\gamma_1$ ($\gamma_1 = (D_{01} + D_{00})/2$), and then calculating by analogy $\gamma_2, \gamma_3, \gamma_4$ and $\gamma_5$;

(3) starting a confining pressure loading system 10 to inject fluid into the confining pressure loading chamber 4, and simultaneously opening an exhaust valve 5 and then closing the exhaust valve 5 until the fluid fills the confining pressure loading chamber 4, loading a confining pressure to a predetermined value, and keeping the confining pressure unchanged;

(4) starting an axial pressure servo motor 13 to apply a bias voltage to the sample 3 to a predetermined value, and keeping the bias voltage constant;

(5) recording an axial displacement amount $l_0, l_1, l_2 \ldots, l_{10}$, and a lateral displacement amount $d_0, d_1, d_2 \ldots, d_{10}$ of respective measuring points 19 of the sample 3 when the sample 3 is stabilized after deformation, the calculation method being the same as in step (2), and calculating an axial deformation amount $L_1, L_2, L_3, L_4, L_5$, a lateral deformation amount $D_1, D_2, D_3, D_4, D_5$, and a value $F_1$ of the pressure testing device at this time by analogy;

obtaining therefore an axial strain $\varepsilon_1$ and a lateral strain $\varepsilon_3$ of respective segments of the sample under non-porous pressure loading which are respectively:

$\varepsilon_1' = (L_1 - \lambda_1)/\lambda_1$, $\varepsilon_1'' = (L_2 - \lambda_2)/\lambda_2$, and $\varepsilon_1'''$, $\varepsilon_1''''$, $\varepsilon_1'''''$ can be obtained in the same way; and $\varepsilon_3' = (D_1 - \gamma_1)/\gamma_3$, $\varepsilon_3'' = (D_2 - \gamma_2)/\gamma_2$, and $\varepsilon_3'''$, $\varepsilon_3''''$ and $\varepsilon_3'''''$ can be obtained in the same way;

according to the formula $$\varepsilon_1 = \frac{(\sigma_1 - 2\mu\sigma_3)}{E}, \varepsilon_3 = \frac{[\sigma_3 - \mu(\sigma_1 + \sigma_3)]}{E},$$

the effective stress of the five segments of the sample can be calculated in sequence, namely $(\sigma_1', \sigma_3'), (\sigma_1'', \sigma_3''), (\sigma_1''', \sigma_3'''), (\sigma_1'''', \sigma_3''''),$ and $(\sigma_1''''', \sigma_3''''')$, where E is Young's modulus and $\mu$ is Poisson's ratio;

(6) starting the pore pressure loading system 12 to inject fluid into the sample 3, so as to increase the injection pressure, and recording a pore pressure value $P_1$ at an inlet end of the sample 3;

(7) recording a pressure $P_2$ in a water storage chamber 16 and a value $F_2$ of the pressure testing device 15 by a flow pressure sensor 8 after a water pressure in the water storage chamber 16 is stabilized, which gradually increases due to the hysteresis of fluid flowing in the sample 3 when adjusting the pore pressure loading system 12 to inject fluid into the sample 3;

(8) obtaining a seepage force measurement value of the core by $J=F_1-F_2$;

(9) calculating a seepage force according to a seepage force calculation formula $J'=r_w \cdot i \cdot V$, where $$i = \frac{h_1 - h_2}{l},$$

$P_1=r_w \cdot h_1$, $P_2=r_w \cdot h_2$, where $r_w$ is volume weight of water, i is pressure gradient, V is sample volume, and $h_1$ and $h_2$ are water heads corresponding to $P_1$ and $P_2$, respectively;

(10) obtaining the seepage force of J under the corresponding axial pressure, confining pressure and flow pressure gradient of the sample 3 when $$\left| \frac{J' - J}{J} \right| < 0.01;$$

otherwise, repeating step (1) to step (9);

(11) recording and calculating an axial deformation data $L_1'$, $L_2'$ ..., $L_5'$, and a lateral deformation data $D_1'$, $D_2'$ ..., $D_5'$ of respective segments corresponding to respective measuring points of the sample 3, the calculation method being the same as in step (2);

(12) obtaining therefore an axial strain $\varepsilon_{11}$ and a lateral strain $\varepsilon_{33}$ of respective segments of the sample in the process of pore pressure loading which are respectively:

$\varepsilon_{11}'=(L_1'-\lambda_1)/\lambda_1$, $\varepsilon_{11}''=(L_2'-\lambda_2)/\lambda_2$, and $\varepsilon_{11}'''$, $\varepsilon_{11}''''$, $\varepsilon_{11}'''''$ can be obtained in the same way; and $\varepsilon_{33}'=(D_1'-\gamma_1)/\gamma_1$, $\varepsilon_{33}''=(D_2'-\gamma_2)/\gamma_2$, and $\varepsilon_{33}'''$, $\varepsilon_{33}''''$, $\varepsilon_{33}'''''$ can be obtained in the same way;

similarly, the effective stress of each of the five measuring segments in the presence of fluid in the pore can be calculated in sequence by formula $$\varepsilon_1 = \frac{(\sigma_1 - 2\mu\sigma_3)}{E}, \quad \varepsilon_3 = \frac{[\sigma_3 - \mu(\sigma_1 + \sigma_3)]}{E},$$

which are respectively $(\sigma_{11}', \sigma_{33}')$, $(\sigma_{11}'', \sigma_{33}'')$, $(\sigma_{11}''', \sigma_{33}''')$, $(\sigma_{11}'''', \sigma_{33}'''')$, and $(\sigma_{11}''''', \sigma_{33}''''')$, and

(13) curve-fitting an increment of the effective stress of respective measuring segments corresponding to respective measuring points 19 generated by the seepage force, by the following formula, respectively:

$\sigma_{axial}'=\sigma_{11}'-\sigma_1'$, $\sigma_{radical}'=\sigma_{33}'-\sigma_3'$;

$\sigma_{axial}''=\sigma_{11}''-\sigma_1''$, $\sigma_{radical}''=\sigma_{33}''-\sigma_3''$;

$\sigma_{axial}'''=\sigma_{11}'''-\sigma_1'''$, $\sigma_{radical}'''=\sigma_{33}'''-\sigma_3'''$;

$\sigma_{axial}''''=\sigma_{11}''''-\sigma_1''''$, $\sigma_{radical}''''=\sigma_{33}''''-\sigma_3''''$;

$\sigma_{axial}'''''=\sigma_{11}'''''-\sigma_1'''''$, $\sigma_{radical}'''''=\sigma_{33}'''''-\sigma_3'''''$;

according to the effective stress obtained in step (13), so as to determine an effective stress change law of at different positions the sample 3 under the seepage force of J.

According to the measuring method of the present invention, the sample 3 is pressurized by the pore pressure loading system 12, and the magnitude of the seepage force and the amount of deformation of different parts of the sample 3 before and after the pore pressure loading are simultaneously observed to obtain the effective stress distribution inside the sample 3 before and after the pore pressure loading. The influence of the seepage force on the effective stress of the sample 3 is obtained by the method of effective stress subtraction.

The above are merely preferred embodiments of the present invention and are not intended to limit the present invention. Therefore, any modification, equivalent substitution and improvement made by using the contents of the present specification and drawings should be included within the protection scope of the present invention.

What is claimed is:

1. A device for measuring the magnitude of a seepage force and its influence on effective stress of a formation, comprising:
    a lower bearing platform having a pressure testing device fixed on an upper part thereof;
    a water storage chamber mounted with a seepage water discharge pipe; and
    a terminal control system;
    wherein a confining pressure loading chamber is mounted on the upper part of the lower bearing platform and a non-contact three-dimensional deformation measuring system is mounted outside the confining pressure loading chamber; the lower bearing platform is used for placing a sample with 11 measuring points distributed at equal intervals on an outer wall thereof;
    an upper permeable pressure-bearing steel sheet and a lower permeable pressure-bearing steel sheet are placed on an upper and a lower end surface of the sample, respectively; the sample is placed inside a transparent rubber sleeve; a top of the upper permeable pressure-bearing steel sheet is provided with an axial pressure loading device connected with an axial pressure servo motor; the upper permeable pressure-bearing steel sheet is respectively connected with a vacuum pump and a pore pressure loading system through a steel pipe line; the confining pressure loading chamber is connected with a confining pressure loading system through a steel pipe line and a transparent observation window is arranged in one side of an outer wall of the confining pressure loading chamber; and
    the axial pressure servo motor, the confining pressure loading system, the pore pressure loading system, the vacuum pump, the non-contact three-dimensional deformation measuring system, a flow pressure sensor and the pressure testing device are all electrically connected with the terminal control system.

2. The device for measuring the magnitude of the seepage force and its influence on the effective stress of the formation according to claim 1, wherein the seepage water discharge pipe is equipped with a valve.

3. The device for measuring the magnitude of the seepage force and its influence on the effective stress of the formation according to claim 1, wherein the confining pressure loading chamber is composed of an outer wall and an end cover, and the end cover is provided with an exhaust valve.

4. The device for measuring the magnitude of the seepage force and its influence on the effective stress of the formation according to claim 1, wherein valves are installed on the steel pipe lines connected with the pore pressure loading system, the confining pressure loading system and the vacuum pump.

5. A method for measuring the magnitude of a seepage force and its influence on effective stress of a formation, comprising the following steps:

(1) taking underground cores with a drilling tool, selecting a core with a complete structure and processing it into a cylindrical sample with a diameter of 50 cm and a height of 100 cm, placing the sample in a confining pressure loading chamber, marking 11 points at equal intervals from top to bottom on an outer wall of the sample as measuring points, placing an upper permeable pressure-bearing steel sheet and a lower permeable pressure-bearing steel sheet having the radius as the sample on the top and bottom of the sample, respectively, and then sleeving the sample into a transparent rubber sleeve;

(2) turning on a vacuum pump to vacuumize the sample for two hours, then turning off the vacuum pump, and recording an axial initial data $L_{00}$, $L_{01}$, $L_{02}$ . . . , $L_{10}$, and a lateral initial data $D_{00}$, $D_{01}$, $D_{02}$ . . . , $D_{10}$ of respective measuring points of the sample through a non-contact three-dimensional deformation measuring system; dividing the 11 measuring points into 5 segments, calculating an axial initial amount of each segment $\lambda_1$ ($\lambda_1 = L_{01} - L_{00}$), and then calculating by analogy $\lambda_2$, $\lambda_3$, $\lambda_4$ and $\lambda_5$, and calculating a lateral initial amount of each segment $\gamma_1$ ($\gamma_1 = (D_{01} + D_{00})/2$), and then calculating by analogy $\gamma_2$, $\gamma_3$, $\gamma_4$ and $\gamma_5$;

(3) starting a confining pressure loading system to inject fluid into the confining pressure loading chamber, and simultaneously opening an exhaust valve and then closing the exhaust valve until the fluid fills the confining pressure loading chamber, loading a confining pressure to a predetermined value, and keeping the confining pressure unchanged;

(4) starting an axial pressure servo motor to apply a bias voltage to the sample to a predetermined value, and keeping the bias voltage constant;

(5) recording an axial displacement amount $l_0$, $l_1$, $l_2$ . . . , $l_{10}$, and a lateral displacement amount $d_0$, $d_1$, $d_2$ . . . , $d_{10}$ of respective measuring points of the sample when the sample is stabilized after deformation, the calculation method being the same as in step (2), and calculating an axial deformation amount $L_1$, $L_2$, $L_3$, $L_4$, $L_5$, a lateral deformation amount $D_1$, $D_2$, $D_3$, $D_4$, $D_5$, and a value $F_1$ of the pressure testing device at this time by analogy;

obtaining therefore an axial strain $\varepsilon_1$ and a lateral strain $\varepsilon_3$ of respective segments of the sample under non-porous pressure loading which are respectively:

$\varepsilon_1' = (L_1 - \lambda_1)/\lambda_1$, $\varepsilon_1'' = (L_2 - \lambda_2)/\lambda_2$, and $\varepsilon_1'''$, $\varepsilon_1''''$, $\varepsilon_1'''''$ can be obtained in the same way; and $\varepsilon_3' = (D_1 - \gamma_1)/\gamma_1$, $\varepsilon_3'' = (D_2 - \gamma_2)/\gamma_2$, $\varepsilon_3'''$, $\varepsilon_3''''$ and $\varepsilon_3'''''$ can be obtained in the same way;

according to the formula $$\varepsilon_1 = \frac{(\sigma_1 - 2\mu\sigma_3)}{E}, \varepsilon_3 = \frac{[\sigma_3 - \mu(\sigma_1 + \sigma_3)]}{E},$$

the effective stress of the five segments of the sample can be calculated in sequence, namely ($\sigma_1'$, $\sigma_3'$), ($\sigma_1''$, $\sigma_3''$), ($\sigma_1'''$, $\sigma_3'''$), ($\sigma_1''''$, $\sigma_3''''$), and ($\sigma_1'''''$, $\sigma_3'''''$), where E is Young's modulus and is Poisson's ratio;

(6) starting the pore pressure loading system to inject fluid into the sample, so as to increase the injection pressure, and recording a pore pressure value $P_1$ at an inlet end of the sample;

(7) recording a pressure $P_2$ in a water storage chamber and a value $F_2$ of the pressure testing device by a flow pressure sensor after a water pressure in the water storage chamber is stabilized, which gradually increases due to the hysteresis of fluid flowing in the sample when adjusting the pore pressure loading system to inject fluid into the sample;

(8) obtaining a seepage force measurement value of the core by $J = F_1 - F_2$;

(9) calculating a seepage force according to a seepage force calculation formula $J' = r_w \cdot i \cdot V$, where $$i = \frac{h_1 - h_2}{l},$$

$P_1 = r_w \cdot h_1$, $P_2 = r_w \cdot h_2$, where $r_w$ is volume weight of water, i is pressure gradient, V is sample volume, and $h_1$ and $h_2$ are water heads corresponding to $P_1$ and $P_2$, respectively;

(10) obtaining the seepage force of J under the corresponding axial pressure, confining pressure and flow pressure gradient of the sample when $$\left|\frac{J' - J}{J}\right| < 0.01;$$

otherwise, repeating step (1) to step (9);

(11) recording and calculating an axial deformation data $L_1'$, $L_2'$ . . . , $L_5'$, and a lateral deformation data $D_1'$, $D_2'$ . . . , $D_5'$ of respective segments corresponding to respective measuring points of the sample, the calculation method being the same as in step (2);

(12) obtaining therefore an axial strain $\varepsilon_{11}$ and a lateral strain $\varepsilon_{33}$ of respective segments of the sample in the process of pore pressure loading which are respectively:

$\varepsilon_{11}' = (L_1' - \lambda_1)/\lambda_1$, $\varepsilon_{11}'' = (L_2' - \lambda_2)/\lambda_2$, and $\varepsilon_{11}'''$, $\varepsilon_{11}''''$, $\varepsilon_{11}'''''$ can be obtained in the same way; and $\varepsilon_{33}' = (D_1' - \gamma_1)/\gamma_1$, $\varepsilon_{33}'' = (D_2' - \gamma_2)/\gamma_2$, and $\varepsilon_{33}'''$, $\varepsilon_{33}''''$, $\varepsilon_{33}'''''$ can be obtained in the same way;

similarly, the effective stress of each of the five measuring segments in the presence of fluid in the pore can be calculated in sequence by formula $$\varepsilon_1 = \frac{(\sigma_1 - 2\mu\sigma_3)}{E}, \varepsilon_3 = \frac{[\sigma_3 - \mu(\sigma_1 + \sigma_3)]}{E},$$

which are respectively ($\sigma_{11}'$, $\sigma_{33}'$), ($\sigma_{11}''$, $\sigma_{33}''$), ($\sigma_{11}'''$, $\sigma_{33}'''$), ($\sigma_{11}''''$, $\sigma_{33}''''$), and ($\sigma_{11}'''''$, $\sigma_{33}'''''$); and

(13) curve-fitting an increment of the effective stress of respective measuring segments corresponding to respective measuring points generated by the seepage force, by the following formula, respectively:

$\sigma_{axial}' = \sigma_{11}' - \sigma_1'$, $\sigma_{radical}' = \sigma_{33}' - \sigma_3'$;

$\sigma_{axial}'' = \sigma_{11}'' - \sigma_1''$, $\sigma_{radical}'' = \sigma_{33}'' - \sigma_3''$;

$\sigma_{axial}''' = \sigma_{11}''' - \sigma_1'''$, $\sigma_{radical}''' = \sigma_{33}''' - \sigma_3'''$;

$\sigma_{axial}''''=\sigma_{11}''''-\sigma_{1}''''$, $\sigma_{radical}''''=\sigma_{33}''''-\sigma_{3}''''$;

$\sigma_{axial}'''''=\sigma_{11}'''''-\sigma_{1}'''''$, $\sigma_{radical}'''''=\sigma_{33}'''''-\sigma_{3}'''''$.

according to the effective stress obtained in step (13), so as to determine an effective stress change law of at different positions the sample under the seepage force of J.

* * * * *